US006794024B1

(12) United States Patent
Walton et al.

(10) Patent No.: US 6,794,024 B1
(45) Date of Patent: Sep. 21, 2004

(54) STYRENIC BLOCK COPOLYMER BREATHABLE ELASTOMERIC FILMS

(75) Inventors: Glynis Allicia Walton, Roswell, GA (US); Richard Macferran Shane, Lilburn, GA (US); Glen Thomas Mildenhall, Marietta, GA (US); Michael Thomas Heffelfinger, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 152 days.

(21) Appl. No.: 09/696,735

(22) Filed: Oct. 25, 2000

Related U.S. Application Data (63) Continuation-in-part of application No. 09/685,070, filed on Oct. 10, 2000, now abandoned.
(60) Provisional application No. 60/162,649, filed on Nov. 1, 1999.

(51) Int. Cl.$^7$ ............................. B32B 5/22; B32B 27/00
(52) U.S. Cl. .................................... 428/317.9; 428/500
(58) Field of Search .......................... 428/317.9, 424.4, 428/424.8, 516, 500

(56) References Cited

U.S. PATENT DOCUMENTS

| | | |
|---|---|---|
| 3,046,172 A | 7/1962 | Reid |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,844,865 A | 10/1974 | Elton et al. |
| 3,849,241 A | 11/1974 | Butin et al. |
| 3,855,046 A | 12/1974 | Hansen et al. |
| 4,041,203 A | 8/1977 | Brock et al. |
| 4,265,960 A | 5/1981 | Arbit et al. |
| 4,340,563 A | 7/1982 | Appel et al. |
| 4,364,985 A | 12/1982 | Tokuyama et al. |
| 4,374,888 A | 2/1983 | Bornslaeger |
| 4,443,513 A | 4/1984 | Meitner et al. |
| 4,472,328 A | 9/1984 | Sugimoto et al. |
| 4,522,203 A | 6/1985 | Mays |
| 4,533,510 A | 8/1985 | Nissel |
| 4,663,220 A | 5/1987 | Wisneski et al. |
| 4,720,415 A | 1/1988 | Vander Wielen et al. |
| 4,734,324 A | 3/1988 | Hill |
| 4,758,239 A | 7/1988 | Yeo et al. |
| 4,777,073 A | 10/1988 | Sheth |
| 4,789,699 A | 12/1988 | Kieffer et al. |
| 4,795,668 A | 1/1989 | Krueger et al. |
| 4,923,650 A | 5/1990 | Antoon, Jr. et al. |
| 4,965,122 A | 10/1990 | Morman |
| 5,011,698 A | 4/1991 | Antoon, Jr. et al. |
| 5,057,368 A | 10/1991 | Largman et al. |
| 5,064,802 A | 11/1991 | Stevens et al. |
| 5,069,970 A | 12/1991 | Largman et al. |
| 5,108,820 A | 4/1992 | Kaneko et al. |
| 5,116,662 A | 5/1992 | Morman |
| 5,164,258 A | 11/1992 | Shida et al. |
| 5,176,953 A | 1/1993 | Jacoby et al. |
| 5,178,931 A | 1/1993 | Perkins et al. |
| 5,188,885 A | 2/1993 | Timmons et al. |
| 5,204,429 A | 4/1993 | Kaminsky et al. |
| 5,271,883 A | 12/1993 | Timmons et al. |
| 5,277,976 A | 1/1994 | Hogle et al. |
| 5,288,791 A | 2/1994 | Collier, IV et al. |
| 5,332,613 A | 7/1994 | Taylor et al. |
| 5,336,545 A | 8/1994 | Morman |
| 5,336,552 A | 8/1994 | Strack et al. |
| 5,374,696 A | 12/1994 | Rosen et al. |
| 5,382,400 A | 1/1995 | Pike et al. |
| 5,393,599 A | 2/1995 | Quantrille et al. |
| 5,451,450 A | 9/1995 | Erderly et al. ............... 428/220 |
| 5,466,410 A | 11/1995 | Hills |
| 5,472,775 A | 12/1995 | Obijeski et al. |
| 5,489,469 A | 2/1996 | Kobayashi et al. |
| 5,539,124 A | 7/1996 | Etherton et al. |
| 5,540,976 A | 7/1996 | Shawver et al. |
| 5,540,992 A | 7/1996 | Marcher et al. |
| 5,554,775 A | 9/1996 | Krishnamurti et al. |
| 5,599,420 A | 2/1997 | Yeo et al. |
| 5,650,225 A | 7/1997 | Dutta et al. |
| 5,691,034 A | 11/1997 | Krueger et al. |
| 5,695,868 A | 12/1997 | McCormack |
| 5,723,546 A | 3/1998 | Sustic |
| 5,733,628 A | 3/1998 | Pelkie |
| 5,759,926 A | 6/1998 | Pike et al. |
| 5,910,136 A | 6/1999 | Hetzler et al. |
| 5,984,911 A | 11/1999 | Siebers et al. |
| 6,015,764 A | 1/2000 | McCormack et al. ........ 442/370 |
| 6,258,308 B1 | 7/2001 | Brady et al. .............. 264/210.2 |
| 6,479,154 B1 | 11/2002 | Walton et al. ............ 428/424.4 |

FOREIGN PATENT DOCUMENTS

| | | |
|---|---|---|
| WO | WO 96/19346 A2 | 6/1996 |
| WO | WO 96/19346 A3 | 6/1996 |
| WO | WO 97/04955 | 2/1997 |
| WO | WO 98/23804 | 6/1998 |
| WO | WO 98/29480 | 7/1998 |
| WO | WO 98/58799 | 12/1998 |
| WO | 99/14039 | 3/1999 |
| WO | 99/14044 | 3/1999 |
| WO | 99/14046 | 3/1999 |
| WO | WO 99/14262 | 3/1999 |
| WO | 99/47590 | 9/1999 |
| WO | 99/49833 | 10/1999 |
| WO | 00/69615 | 11/2000 |

OTHER PUBLICATIONS

Kirk–Othmer, *Encyclopedia of Chemical Technology, Fourth Edition*, John Wiley & Sons, Inc., New York, vol. 17, 765–767, 1996.

*Primary Examiner*—Terrel Morris
*Assistant Examiner*—Hai Vo
(74) *Attorney, Agent, or Firm*—Pauley Petersen & Erickson (57) ABSTRACT

A breathable, elastic film including a high performance elastomer, such as a styrenic copolymer, and a low performance elastomer, such as a polyolefin, filled with a plurality of particles suitable for forming pores in the film upon stretch-thinning of the film, the film having been stretch-thinned, whereby the low performance elastomer portion of the film forms a plurality of micropores. Also disclosed are laminates employing this breathable, elastic film.

10 Claims, 2 Drawing Sheets

STYRENIC BLOCK COPOLYMER BREATHABLE ELASTOMERIC FILMS

CROSS REFERENCE TO RELATED APPLICATION

This application claims the benefit of U.S. Provisional Application No. 60/162,649 filed Nov. 01, 1999 and is a continuation-in-part application of U.S. patent application Ser. No. 09/685,070 filed Oct. 10, 2000, now abandoned.

FIELD OF THE INVENTION

This invention is related to a breathable elastomeric film made from high performance elastomers such as styrenic block copolymers and filled low performance elastomers such as polyolefins, and a soft, breathable elastic laminate comprising said breathable elastomeric film and a nonwoven web. The laminate is particularly useful as an outer cover for disposable diapers and other disposable personal care products, and for breathable surgical gowns and other breathable by applications. In addition, this invention is directed to a method for producing such films and laminates.

BACKGROUND OF THE INVENTION

The present invention is directed to breathable elastomeric films and nonwoven materials and laminates thereof. Such laminates have a wide variety of uses, particularly in the areas of limited use and disposable items.

Films have been traditionally used to provide barrier properties in limited use or disposable items. By limited use or disposable, it is meant that the product and/or component is used only a small number of times, or possibly only once, before being discarded. Examples of such products include, but are not limited to, surgical and health care related products such as surgical drapes and gowns, disposable work wear such as coveralls and lab coats, and personal care absorbent products such as diapers, training pants, incontinence garments, sanitary napkins, bandages, wipes and the like. In personal care absorbent products, such as infant diapers and adult incontinence products, films are used as the outer covers so as to prevent body wastes from contaminating the clothing, bedding and other aspects of the surrounding environment of use. In protective apparel, such as hospital gowns, films are used to prevent cross-exchange of microorganisms between the wearer and the patient.

Although these films are generally effective barriers with respect to water vapor and the like, they are not aesthetically pleasing because their surfaces are smooth and either feel slick or tacky and they are visually unappealing, making them less desirable in apparel applications and other uses where they are in contact with human skin. Thus, it is desirable that these items be more cloth-like, both from a tactile and visual standpoint. It is also desirable for an outer cover material to possess stretch and recovery properties to provide better fit and comfort. It is particularly desirable that the stretch and recovery properties be biaxial to accommodate the movement of the wearer in different directions.

Laminates of films have been used to create materials which are both impervious and somewhat cloth-like in appearance and texture. One example of such a laminate is the outer cover on disposable diapers. A primary purpose of the film in such laminates is to provide barrier properties. However, there is also a need that such laminates be breathable so that they can transmit water vapor which, in turn, requires that the film be breathable. Apparel made from laminates of breathable or microporous films are more comfortable to wear because they reduce the water vapor concentration and the consequent skin hydration underneath the apparel item.

There are a number of known ways of making a film breathable including aperturing and the use of fillers. Breathable polyolefin films can be produced by stretching a precursor film filled with a filler such as calcium carbonate particles. Breathable films which are gas/vapor permeable and liquid impermeable are taught by U.S. Pat. No. 4,472,328 to Sugimoto et al. The Sugimoto et al. patent teaches a breathable polyolefin film prepared from a polyolefin/filler composition having from 20 percent to 80 percent by weight of a filler such as a surface treated calcium carbonate. A liquid or waxy hydrocarbon polymer elastomer was found to produce a precursor film that could be monoaxially or biaxially stretched to make the film breathable. U.S. Pat. No. 4,777,073 to Sheth teaches a breathable film produced from a precursor film that is prepared from a polymer composition comprising at least one polyolefin component and a filler. Suitable polyolefins for film production are indicated to include polypropylene, copolymers of propylene, homopolymers and copolymers of ethylene or blends thereof. Suitable fillers are indicated to be any organic or inorganic material having a low affinity for and a significantly lower elasticity than the polyolefin component, or no elasticity at all, preferably a rigid material having a non-smooth hydrophobic surface or a material which is treated to render its surface hydrophobic.

Laminates or composites of breathable films and nonwoven materials are taught by U.S. Pat. No. 5,695,868 to McCormack. The laminates or composites are made from a breathable film which is stretch-thinned and bonded to a fibrous polyolefin nonwoven web.

PCT International Patent Publication No. WO 99/14044 teaches a soft, breathable elastic laminate comprising a water vapor impermeable, or water vapor mu permeable, elastic film material loaded with a filler having a particle size suitable for pore formation and a nonwoven web bonded to the elastic film, the film being stretched in at least two directions. The stretching of the film renders the film microporous and, thus, breathable, or, in the case of films which are initially breathable, more breathable. The breathable elastomeric film is a metallocene-catalyzed polyethylene polymeric resin material comprising a filler material of at least 10% by volume of the film. The metallocene-catalyzed polyethylene polymeric resin material has a density of from about 0.850 to about 0.917 g/cc, and the film comprises from about 10% by volume to about 50% by volume filler. Although having good elastic properties, a film having better elastic properties than metallocene-catalyzed polyethylene elastomers is desirable.

One such film is disclosed by U.S. Pat. No. 5,733,628 to Pelkie which teaches breathable, elastic polymeric film laminates employing apertured films made from high performance elastomeric materials such as styrene block copolymers.

One problem which has been found when using filled elastomers for producing breathable stretch-thinned films is the tendency of the micropores formed during the stretch-thinning process to close up upon release of the stretching force due to the elastic recovery properties of the elastomers. This is particularly true of high performance elastomers like styrene block copolymers. As a result, there has always been a tradeoff between breathability and stretch and recovery properties for stretch-thinned filled elastic materials.

SUMMARY OF THE INVENTION

Accordingly, it is one object of this invention to provide a film capable of high breathability and high elastic stretch and recovery once it is stretch-thinned.

It is another object of this invention to provide a film having high breathability and high elastic stretch and recovery which is capable of high biaxial stretching.

These and other objects of this invention are addressed by a breathable elastic film comprising a blended or compounded product formed by blending or compounding a high performance elastomer and a filled low performance elastomer, the filler including a plurality of particles suitable for forming pores in the film upon stretch-thinning of the film. In accordance with a particularly preferred embodiment of this invention, the high performance elastomer is a styrenic block copolymer and the low performance elastomer is a polyolefin. Upon stretch-thinning of the film, micropores are formed by the low performance elastomer portion of the film. In accordance with one embodiment of this invention, the high performance elastomer is also filled with particles suitable for pore formation whereby, upon stretch-thinning of the film, micropores are formed by both the high performance elastomer portion and the low performance elastomer portion of the film. The microporous stretch-thinned film of this invention demonstrates both high breathability as well as elastic stretch properties greater than 100 percent and recovery.

In accordance with one embodiment of the invention, the microporous film is laminated to a fibrous layer. The fibrous layer can comprise a nonwoven web such as, for example, an extensible nonwoven web. Film/nonwoven laminates of the present invention can be used as a barrier layer in personal care articles such as, for example, as outer covers in diapers, adult incontinence garments, protective apparel and the like. In addition, the breathable microporous films and/or film laminates of this invention can comprise a component of an absorbent bodily article. As one example, an absorbent bodily article can comprise a liquid pervious liner; an absorbent core; and a microporous film or film laminate of this invention wherein the absorbent core is positioned between the liquid pervious liner and microporous film or film laminate.

The films of this invention are produced by blending or compounding a high performance elastomer with a low performance elastomer, at least one of which is filled with particles suitable for pore formation upon stretching of the film, forming a blended or compounded product, forming the blended or compounded product into a filled film and stretch-thinning the film, forming a plurality of micropores in at least one of the high performance elastomer portion and the low performance elastomer portion of the film.

In accordance with one particularly preferred embodiment, the films of this invention are produced by blending or compounding a filled styrenic block copolymer with a filled polyolefin, forming a blended or compounded product, forming the blended or compounded product into a filled film comprising a well dispersed blend of styrenic block copolymer and the polyolefin, and stretch-thinning the film, forming a plurality of micropores throughout the stretch-thinned film.

DESCRIPTION OF PREFERRED EMBODIMENTS

Definitions

As used herein, the term "comprising" is inclusive or open-ended and does not exclude additional unrecited elements, compositional components, or method steps.

As used herein, the term "recover" refers to a contraction of a stretched material upon termination of a biasing force following stretching of the material by application of the biasing force. For example, if a material having a relaxed, unbiased length of 1 in. (2.5 cm) is elongated fifty percent by stretching to a length of 1½ in. (3.75 cm), the material would be elongated 50 percent and would have a stretched length of 1.5×. If this exemplary stretched material contracted, that is recovered to a length of 1$\frac{1}{10}$ inches (2.75 cm) after release of the biasing and stretching force, the material would have recovered 80 percent of its ½ inch (1.25 cm) elongation. Percent recovery may be expressed as [(maximum stretch length–final sample length)/(maximum stretch length–initial sample length)]×100.

As used herein, the term "nonwoven web" means a web that has a structure of individual fibers or threads which are interlaid, but not in an identifiable repeating manner. Nonwoven webs have been, in the past, formed by a variety of processes such as, for example, meltblowing processes, spunbonding processes, coforming processes, hydroentangling, air-laid and bonded carded web processes.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 25 percent greater than its relaxed unbiased length, and that will cause the material to recover at least 40 percent of its elongation upon release of the stretching elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, and many of these will recover to substantially their original relaxed length upon release of the stretching, elongating force.

As used herein, the term "percent stretch" refers to the ratio determined by measuring the increase in the stretched dimension and dividing that value by the it, original dimension, i.e. (increase in stretched dimension/original dimension)×100.

As used herein, the term "ultimate elongation" should be understood to mean a predefined elongation percentage.

As used herein, the term "set" refers to retained elongation in a material sample following the elongation and recovery, i.e after the material has been stretched and allowed to relax.

As used herein, the term "percent set" is the measure of the amount of the material stretched from its original length after being cycled. The remaining strain after the removal of the applied stress is measured as the percent set. The percent set is where the retraction curve of a cycle crosses the elongation axis, and as further discussed below.

As used herein, the term "machine direction" or "MD" means the length of a fabric in the direction in which it is produced. The term "cross machine direction" or "CD" means the width of fabric, that is a direction generally perpendicular to the MD.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10 fibers) larger than 7 microns, more particularly, between about 10 and 30 microns. The fibers may also have shapes such as those described in U.S. Pat. No. 5,277,976 to Hogle et al., U.S. Pat. No. 5,466,410 to Hills, and U.S. Pat. Nos. 5,069,970 and 5,057,368 to Largman et al., which describe hybrids with unconventional shapes. A nonwoven web of spunbond fibers produced by melt spinning is referred to as a "spunbond".

As used herein, the term "meltblown fibers" means fibers formed by extruding a molten thermoplastic material through a plurality of fine, usually circular, die capillaries as molten threads or filaments into converging high velocity, usually hot, gas (for example, air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, by U.S. Pat. No. 3,849,241 to Butin et al. Meltblown fibers are microfibers which may be continuous or discontinuous, and are generally smaller than 10 microns in average diameter.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" also includes all possible geometric configurations of the molecule. These configurations include, but are not limited to, isotactic, syndiotactic and random symmetries.

As used herein, the term "microfibers" refers to small diameter fibers having an average diameter not greater than about 100 microns, for example, having an average diameter of from about 0.5 microns to about 50 microns, or more particularly, having an average diameter of from about 2 microns to about 40 microns. Another frequently used expression of fiber diameter is denier, which is defined as grams per 9000 meters of a fiber, and may be calculated as fiber diameter in microns squared, multiplied by the density in grams/cc, multiplied by 0.00707. A lower denier indicates a finer fiber and a higher denier indicates a thicker or heavier fiber. For example, a diameter of a polypropylene fiber given as 15 microns may be converted to denier by squaring, multiplying the results by 0.89 g/cc and multiplying by 0.00707. Thus, a 15 micron polypropylene fiber has a denier of about 1.42. Outside the United States, the unit of measurement is more commonly the "tex", which is defined as the grams per kilometer of fiber. Tex may be calculated as denier/9.

As used herein, the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, the term "bicomponent fibers" refers to fibers which have been formed from at least two polymers extruded from separate extruders but spun together to form one fiber. Bicomponent fibers are also sometimes referred to as conjugate fibers or multicomponent fibers. The polymers are arranged in substantially constantly positioned distinct zones across the cross-sections of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger et al., U.S. Pat. No. 5,540,992 to Marcher et al., and U.S. Pat. No. 5,336,552 to Strack et al. Bicomponent fibers are also taught by U.S. Pat. No. 5,382,400 to Pike et al. For two component fibers, the polymers may be present in ratios of 75/25, 50/50, 25/75 or any other desired ratio.

As used herein, the term "personal care absorbent article" means disposable diapers, training pants, absorbent underpants, adult incontinence products, feminine hygiene products including sanitary pads and napkins, wipes, tissues, bandages, dressings and the like.

As used herein, the term "necked" or "necked material" refers to any material which has been constricted in at least one dimension by processes such as, for example, drawing or gathering.

As used herein, the term "neckable material" means any material which can be necked.

As used herein, the term "high performance elastomer" means an elastomer having a level of hysteresis of less than about 75% as determined by the method described below and preferably, less than about 60%. The hysteresis value is determined by first elongating a sample to an ultimate elongation of 50% and then allowing the sample to retract to an amount where the amount of resistance is zero. For the purposes of this application, the term ultimate elongation should be understood to mean a predefined elongation percentage. For the purposes of this application, the hysteresis value determining numbers as used in the definition of high and low performance elastomers, (and as further explained below) are read at the 30 percent and 50 percent total ultimate elongation in the cross-machine direction. High performance elastomers in accordance with this disclosure may be characterized as materials having the elastic properties of styrenic based block copolymers such as those available from the Shell Company under the brand KRATON®.

As used herein, the term "low performance elastomer" means an elastomer having a level of hysteresis of greater than about 75%, determined by the method described below. Low performance elastomers in accordance with this disclosure may be characterized by materials having the elastic properties of polyolefins including metallocene catalyzed polyolefins such as single site metallocene catalyzed linear low density polyethylene.

As used herein, the term "breathable" refers to a material which is permeable to water vapor having a minimum WVTR (water vapor transmission rate) of about 1,000 g/m$^2$/24 hours. The WVTR of a fabric, in one aspect, gives an indication of how comfortable a fabric would be to wear. WVTR is measured as indicated below and the results are reported in grams/square meter/24 hours. However, often applications of breathable barriers desirably have higher WVTRs and breathable barriers of the present invention can have WVTRs exceeding about 1,200 g/m$^2$/24 hours, 1,500 g/m$^2$/24 hours, 1,800 g/m$^2$/24 hours or even exceeding 2,000 g/m$^2$/24 hours.

As used herein, the term "particle size" describes the largest dimension or length of the filler.

As used herein, the term "flexible polyolefin" (FPO) refers to polyolefin materials containing propylene based polymer with controlled regions of atactic polypropylene units to achieve a desired crystallinity such as described in U.S. Pat. No. 5,910,136 entitled "Oriented Polymeric Microporous Films with Flexible Polyolefins and Methods of Making the Same" to Hetzler and Jacobs; the entire contents of which are incorporated herein by reference.

As used herein, the tern "stretchable bicomponent spunbond" (FPO/PP) refers to a material having both MD and CD stretch properties. This material has demonstrated stretch extensions between 50 and 75%, soft hand, fiber crimping at ambient FDU (fiber draw unit) temperature, and the strength of traditional spunbond. Sheet materials have been produced containing polypropylene side by side (S/S) with flexible polyolefins. Polymer ratios can range from 50/50 to 70/30 PP/FPO. While single bank fabrics have been produced, improved properties are expected with layered or two bank materials. The fiber draw unit air supply can range from room temperature to 260° F. Materials have been produced utilizing the Hansen and Pennings bond pattern and Wire Weave bond pattern, with similar properties. The FPO/PP spunbond can be utilized as a stretchable member of a disposable personal care product, such as a diaper liner, diaper outer cover, hook and loop fastener base, a substitute for necked spunbond material, a component of film laminates, and a component of other laminates where stretch and recovery are desired. Stretchable bicomponent spunbond (FPO/PP) can be made in-line in one step. Fabric produced from such process exhibits recovery from stretch due to inherent elasticity. Further description of flexible polyolefins can be found in U.S. Pat. No. 5,723,546 to Sustic and assigned to the Rexene Corporation.

As used herein, polyethylene plastomers or polyolefin plastomers are low density ethylene elastomers which include ethylene copolymers having a density less than about 0.90 grams/cm$^3$, desirably from about 0.86 grams/cm$^3$ to about 0.89 grams/cm$^3$ and even more desirably from about 0.87 grams/c to about 0.88 grams/cm$^3$. Suitably, the ethylene elastomers include linear low density polyethylene. Suitably, the ethylene elastomers include a polymer wherein the ethylene monomers are polymerized with an alpha-olefin such that the resulting polymer compositions have a narrow molecular weight distribution ($M_w/M_n$) of about 2, homogeneous branching, and controlled long chain branching. Suitable alpha-olefins include, but are not limited to, 1-octene, 1-butene, 1-hexene and 4-methyl-pentene. Exemplary polymers include those made by "metallocene," "constrained geometry" or "single-site" catalysts such as those described in U.S. Pat. No. 5,472,775 to Obijeski, et al. U.S. Pat. No. 5,451,450 to Erderly, et al.; U.S. Pat. No. 5,204,429 to Kaminsky, et al.; U.S. Pat. No. 5,539,124 to Etherton, et al.; and U.S. Pat. No. 5,554,775 to Krishnamurti, et al.; each of which is hereby incorporated by reference.

The invention disclosed herein is a breathable, filled elastic film produced by blending or compounding a high performance elastomer and a low performance elastomer, at least one of which is filled with a filler, melt extruding the mix into a film and stretch-thinning the film to create micropores and, thus, breathability. Such high performance elastomers include styrenic based block copolymers such as those available from the Shell Company under the brand KRATON®. In accordance with a particularly preferred embodiment, the high performance elastomer is a styrenic block copolymer, KRATON® G (Shell Chemical Company) and the low performance elastomer is a polyolefin. One preferred polyolefin suitable for use in the film of this invention is AFFINITY®, a single site metallocene catalyzed linear low density polyethylene (LLDPE) available from Dow Chemical Company. Metallocene catalyzed polymers are described in U.S. Pat. No. 5,472,775 to Obijeski et al. and assigned to the Dow Chemical Company, the entire contents of which are incorporated herein by reference. The metallocene process generally uses a metallocene catalyst which is activated, i.e. ionized, by a co-catalyst. Examples of metallocene catalysts include bis(n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow. However, numerous other metallocene, single-site and/or similar catalyst systems are known in the art; see for example, U.S. Pat. No. 5,539,124 to Etherton et al.; U.S. Pat. No. 5,554,775 to Krishnamurti et al.; U.S. Pat. No. 5,451,450 to Erderly et al. and *The Encyclopedia of Chemical Technology*, Kirk-Othemer, Fourth Edition, vol. 17, Olefinic Polymers, pp. 765–767 (John Wiley & Sons 1996); the entire content of the aforesaid patents being incorporated herein by reference. The filler enables development of micropores during stretching of the film. As used throughout the specification and claims, the term "filler" means particulates and other forms of materials which can be added to a polymer or polymers and which will not chemically interfere with or adversely affect the extruded film but are able to be uniformly dispersed throughout the polymer(s) comprising the film. Generally, the fillers are in particulate form and usually have irregular shapes with average particle sizes in the range of about 0.50 to about 8 microns. In addition, the film usually contains in the range of about 10 to 65 weight percent filler based upon the total weight of the film layer.

Both organic and inorganic fillers are suitable for use in this invention provided that they do not interfere with the film formation process, the breathability of the resultant film, or the ability of the film to bond to another layer such as a fibrous polyolefin nonwoven web.

Examples of suitable fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives. In accordance with a particularly preferred embodiment of this invention, the filler is calcium carbonate particles.

The high performance elastomer may constitute about 10–35% by weight of the film. The low performance elastomer may constitute about 5–30% by weight of the film. The filler particles may constitute greater than about 50% by weight of the film. In one embodiment, the film may include about 10–35% by weight of the high performance elastomer, about 5–30% by weight of the low performance elastomer, and about 51–70% by weight of the filler particles.

It has been found that melt blending of a lower performance elastomer such as metallocene catalyzed polyethylene plastomers, low density metallocene single site catalyzed polyolefins with densities of 0.91 g/cc and lower such as AFFINITY PL1845 and EG8200 available from Dow Chemical Company, in the amount of about 10 percent to about 30 percent by weight of the film with KRATON G rubber materials, and concentrations of calcium carbonate in excess of about 50 percent by weight, produces a film capable of high breathability and high elastic stretch and recovery after being stretch-thinned (oriented). Preferred KRATON G resins in accordance with preferred embodiments of this invention are tetrablock and diblock resins. To produce this film, it is preferred that the film precursor be precompounded with calcium carbonate prior to production of the film. However, the KRATON G/calcium carbonate blend and the polyethylene plastomer/calcium carbonate blend may be precompounded separately from each other and then dry blended prior to production of the film. Stretch-thinning of the film is preferably in the range of about 200 to 500 percent of its original length.

In accordance with one embodiment of this invention, the film is laminated to a nonwoven web material such as a spunbond, meltblown or bonded carded web material to produce a breathable laminate which is fluid impermeable, and, thus, suitable for use as an outer cover or liner for personal care absorbent articles such as disposable diapers, training pants, incontinence garments and the like. For a laminate comprising, for example, a breathable film in accordance with this invention laminated to a spunbond, it is necessary for the film to be stretched in the machine direction and then laminated to a CD stretchable spunbond material so as to provide a laminate which is CD stretchable. In order to provide MD stretch as well as CD stretch, the film is preferably laminated to the spunbond while still under stretch tension in the machine direction. After lamination, the film/laminate is allowed to retract fully prior to winding into a roll. This retraction results in bunching of the spunbond which allows the laminate to stretch in the machine direction without being hindered by the spunbond, which typically does not stretch in the machine direction.

Figure 1:
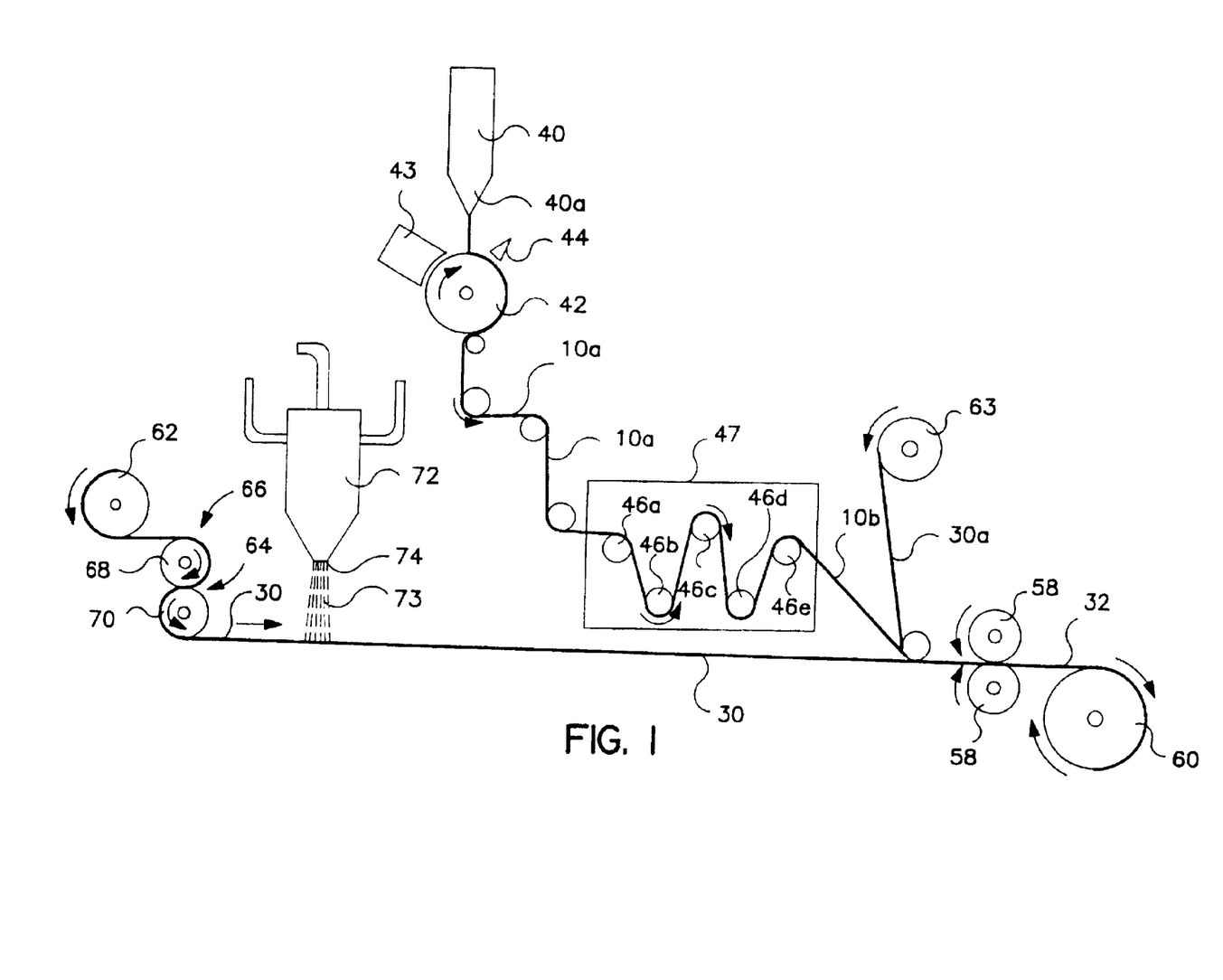
FIG. 1 is a schematic side view of a process for forming a multilayer film according to the present invention and a multilayer film/nonwoven laminate according to the present invention.

A process for forming the product film 10c is shown in FIG. 1 of the drawings. However, before a precursor film 10a is manufactured, the raw materials, i.e. the polymer(s) and filler must first be compounded through a process generally known to those skilled in the art. For instance, the raw materials can be dry mixed together and added into a hopper of a twin screw extruder. In the hopper, the materials are dispersively mixed in the melt and conveyed by the action of the intermeshing rotating screws. Upon exiting the twin screw extruder the material is immediately chilled and cut into pellet form.

Referring again to the figure, the precursor film 10a is formed from a monolayer extrusion film apparatus 40 such as a cast or blown unit. The compounded material is first directed into the film extruder (hoppers).

The film 10a is extruded onto a chill roll 42, which may be patterned. The flow out of the die 40a is immediately cooled on the chill roll 42. A vacuum box 43 situated adjacent the chill roll creates a vacuum along the surface of the roll to help maintain the precursor film 10a lying close to the surface of the roll. Additionally, air knives or electrostatic pinners 44 assist in forcing the precursor film 10a to the chill roll surface as it moves around the spinning roll. An air knife is a device known in the art which focuses a stream of air at a very high flow rate to pin the edges of the film. The result is the creation of a thin film. This thin precursor film 10a may be collected or subjected to further processing.

The precursor film 10a is subjected to further processing to make it breathable. Therefore, from the coextrusion film apparatus 40, the precursor film 10a is directed to a film stretching unit 47, such as a machine direction orienter or "MDO" which is a commercially available device from vendors such as the Marshall and Williams Company of Providence, R.I. This apparatus 47 has a plurality of stretching rollers 46a–e which progressively stretch and thin the multilayer film in the machine direction of the film, which is the direction of travel of the film through the process as shown in FIG. 1. While the MDO is illustrated with five rolls, it should be understood that the number of rolls may be higher or lower depending on the level of stretch that is desired and the degrees of stretching between each roll. The film can be stretched in either single or multiple discrete stretching operations. Desirably, the unstretched filled film (precursor film) will be stretched from about 2 to about 6 times its original length, imparting a set in the stretched film 10b of between 3 to about 5.5 times of the original film length.

Referring again to FIG. 1, heated rolls 46a and 46b may act as preheat rolls. These first few rolls heat the film slightly above room temperature (90° F.). Slow roll 46c travels at a circumferential speed slower than the following fast roll 46d. The different speeds of the adjacent rolls act to stretch the filled precursor film 10a. The rate at which the stretch rolls rotate determines the amount of stretch in the film, and thus the level of breathability. One or both of the slow roll 46c and fast roll 46d can be heated. After stretching, the film 10b may be allowed to slightly retract and/or be further heated or annealed by one or more heated rolls, such as by heated anneal roll 46e. These rolls are typically heated to about 120° F. to anneal the film. After the film exits the MDO, it includes a permanent elongation as compared to the original precursor film. At this point, the stretch-thinned filled product film may be wound for storage or further processed.

If desired, the product film 10b may be attached to one or more support layers 30 to form a film/laminate 32. Suitable laminate materials include nonwoven fabrics, multi-layered nonwoven fabrics, scrims, woven fabrics and other like materials. In order to achieve a laminate with improved body conformance, the fibrous layer is desirably an extensible fabric and even more desirably an elastic fabric. For example, tensioning a nonwoven fabric in the MD causes the fabric to "neck" or narrow in the CD and give the necked fabric CD stretchability. Examples of additional suitable extensible and/or elastic fabrics include, but are not limited to, those described in U.S. Pat. No. 4,443,513 to Meitner et al.; U.S. Pat. No. 5,116,662 to Morman et al.; U.S. Pat. No. 4,965,122 to Morman et al.; U.S. Pat. No. 5,336,545 to Morman et al.; U.S. Pat. No. 4,720,415 to Vander Wielen et al.; U.S. Pat. No. 4,789,699 to Kieffer et al.; U.S. Pat. No. 5,332,613 to Taylor et al.; U.S. Pat. No. 5,288,791 to Collier et al.; U.S. Pat. No. 4,663,220 to Wisneski et al.; U.S. Pat. No. 5,540,976 to Shawver et al. The entire content of the aforesaid patents are incorporated herein by reference. Nonwoven fabrics which are to be laminated to such films desirably have a basis weight between about 10 $g/m^2$ and about 70 $g/m^2$ and even more desirably between about 15 $g/m^2$ and about 34 $g/m^2$. As a particular example, a 17 $g/m^2$ (0.5 ounces per square yard) web of polypropylene spunbond fibers can be necked a desired amount and thereafter laminated to a breathable stretched filled-product film 10b. The product film 10b would therefore be nipped (in lamination rolls of a calender roll assembly) to a necked or CD stretchable spunbond nonwoven web.

The film and spunbond material typically enter the lamination rolls at the same or lower rate as the film exits the MDO. The outer nonwoven layer can be laminated to the breathable filled-product film by one or more means known in the art. The nonwoven layer and filled-film can be bonded, e.g. point bonded, by imparting sufficient energy to the film and/or fibrous fabric to cause the materials to soften and/or flow such as, for example, by applying thermal, ultrasonic, microwave and/or compressive force or energy. Bonding agents or tackifiers may be added to the film to improve adhesion of the layers. In a further aspect of the invention, the filled-film and fibrous layer can be adhesively laminated to one another. In order to achieve improved drape the adhesive is desirably pattern applied to one of the fabrics or applied only to the outer fibrous layer. By applying the adhesive to the outer fibrous layer, such as a nonwoven fabric, the adhesive will generally only overlie the film at fiber contact points and thus provide a laminate with improved drape and/or breathability. Examples of suitable adhesives include, but are not limited to, REXTAC™ 2730 from Huntsman Corporation of Salt Lake City, Utah; H2525A which is a styrene block copolymer adhesive available from Findley Adhesives, Inc. of Wauwatusa, Wis.; and 34-5610 which is a styrene block copolymer adhesive available from National Starch, Starch and Chemical Co. of Bridgewater, N.J. Commercially available amorphous polyalphaolefins (APAO) used in hot melt adhesives suitable for use with the present invention include, but are not limited to, REXTAC™ ethylene-propylene APAO E-4 and E-5 and butylene-propylene BM-4 and BH-5 from Huntsman Corporation of Salt Lake City, Utah, and VESTOPLAST™ 792 from Hüls AG of Marl, Germany. Amorphous polyalphaolefins can be synthesized on a Ziegler-Natta supported catalyst and an alkyl aluminum co-catalyst and the olefin, such as propylene, is polymerized in combination with varied amounts of ethylene, 1-butene, 1-hexane or other materials to produce a predominantly atactic hydrocarbon chain. Desirably, about 1 $g/m^2$ to about 10 $g/m^2$ of adhesive is applied to a fibrous support fabric prior to superposing the support layer and filled-film. Additional bonding aids or tackifiers, can also be used.

Referring again to FIG. 1, a process is shown for creating a three layer laminate from a prefabricated extensible nonwoven material. A stretched filled product film 10b is shown being attached to an extensible fibrous layer 30, such as a necked spunbond web, to form a film/nonwoven laminate. A neckable material 30 is unwound from a supply roll 62. The neckable material 30 then travels in the direction indicated by the arrows associated therewith. The neckable material 30 then passes through the nip 64 of S-roll arrangement 66, formed by a stack of rollers 68 and 70, in a reverse S-wrap path, as indicated by the arrows associated with stack rollers 68 and 70. Because the circumferential or peripheral speed of the rollers of the S-roll arrangement 66 is controlled to be slower than the peripheral line speed of the downline calender roll assembly 58, as seen in FIG. 1, the neckable material 30 is tensioned so that it necks a desired amount. The necked material 30 could alternatively be necked off-line and unrolled in the tensioned, necked condition. The necked material 30 is maintained in the tensioned, necked condition as it passes under spray equipment 72 which sprays an adhesive 73 through adhesive die head 74 into the necked material 30. Once the stretched filled product film 10b has been sufficiently thinned, the necked material 30 formed and adhesive applied thereto, the layers can be brought together and the adhesive treated (if necessary with heat), thereby forming the breathable laminate 32.

Alternatively, a conventional fibrous nonwoven web forming apparatus, such as a pair of spunbond machines, may be used to form the support layer 30 in an in-line process. In such an in-line process, the long, essentially continuous fibers would be deposited onto a forming wire as an unbonded web. The unbonded web would then be sent through a pair of bonding rolls to bond the fibers together and increase the tear strength of the resultant web support layer. One or both of the rolls may be heated to aid in bonding. Typically, one of the rolls is also patterned so as to impart a discrete bond pattern with a prescribed bond surface area to the web. The other roll is usually a smooth anvil roll but this roll also may be patterned if so desired. Once the product film has been sufficiently thinned and oriented and the support layer has been formed, the two layers would then be brought together and laminated to one another using a pair of laminating rolls or other means.

As with bond rolls, the laminating rolls 58 may be heated. Also, at least one of the rolls may be patterned to create a discrete bond pattern with a prescribed bond surface area for the resultant laminate. Generally, the maximum bond point surface area for a given area of surface on one side of the laminate will not exceed about 50 percent of the total surface area. There are a number of discrete bond patterns which may be used such as the H&P bond pattern, the C-star bond pattern or the Baby Object bond pattern. See, for example, Brock et al., U.S. Pat. No. 4,041,203, which is incorporated herein by reference in its entirety. Once the laminate exits the laminating rolls, it would be wound up into a roll for subsequent processing. Alternatively, the laminate may continue in-line for further processing or conversion.

The process shown in FIG. 1 also may be used to create a three layer laminate 32. The only modification to the previously described process is to feed a supply 63 of a second fibrous nonwoven web support layer 30a into the laminating rolls 58 on a side of the product film 10b opposite that of the other fibrous nonwoven web support layer 30. As shown in FIG. 1, the supply of support layer 30 is in the form of a pre-formed roll 62. Alternatively, as with the other layers, the support layer 30 may be formed directly in-line. In either event, the second support layer 30a is fed into the laminating rolls 58 and is laminated to the product film 10b in the same fashion as the first support layer 30.

As has already been stated, once the laminate 32 is produced, the material continues on to the winder. As the material moves to the winder, it is allowed to retract. This is achieved by slowing the speed of the winder to adjust for the retraction of the material. This process allows for machine direction stretch in the material since the spunbond has "bunched up" along with the retracting film and therefore has "give" when stretched in the machine direction in the finished laminate 32.

Figure 2:
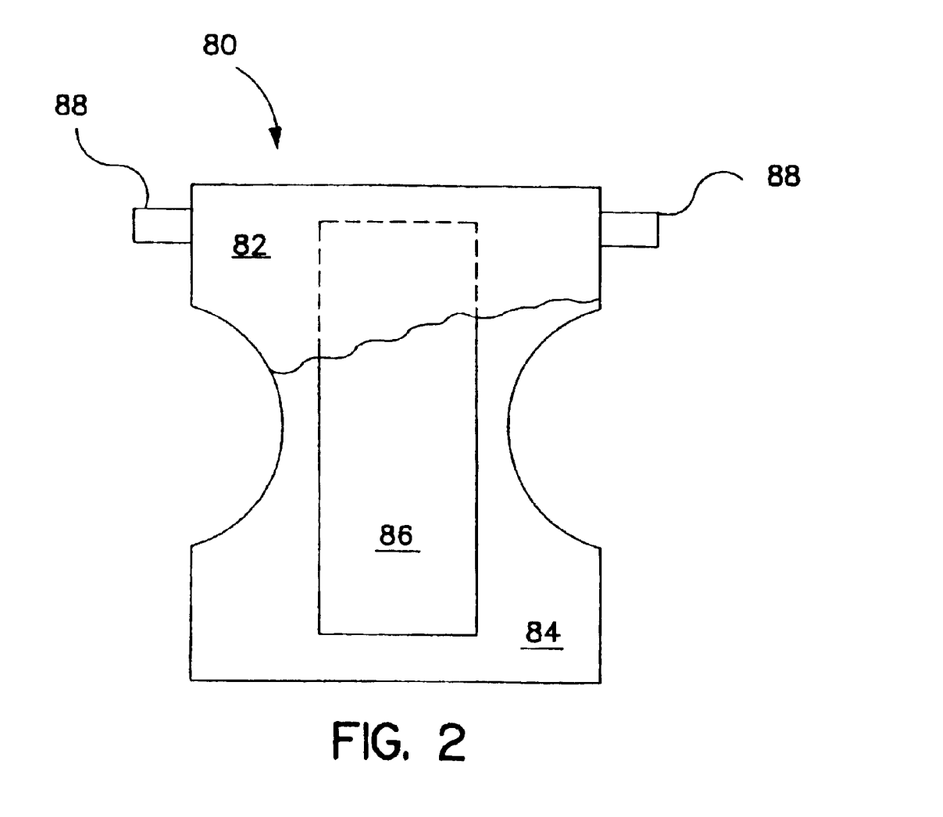
FIG. 2 is a partially cut away top plan view of an exemplary personal care absorbent article, in this case a diaper, which utilizes a multilayer film and multilayer film/nonwoven laminate according to the present invention.

As has been stated previously, the product film 10b in a laminate 32 may be used in a wide variety of applications, not the least of which includes personal care absorbent articles such as diapers, training pants, incontinence devices and feminine hygiene products such as sanitary napkins. An exemplary article 80, in this case a diaper, is shown in FIG. 2 of the drawings. Referring to FIG. 2, most such personal care absorbent articles 80 include a liquid permeable top sheet or liner 82, a back sheet or outercover 84 and an absorbent core 86 disposed between and contained by the top sheet 82 and back sheet 84. Articles 80 such as diapers may also include some type of fastening means 88 such as adhesive fastening tapes or mechanical hook and loop type of fasteners.

The product film 10b by itself, or in other forms, such as the film/support layer laminate 32 may be used to form various portions of the article including, but not limited to, the top sheet 82 and the back sheet 84. If the film is to be used as the liner 82, it will most likely have to be apertured or otherwise made to be liquid permeable. When using a film/nonwoven laminate 32 as the outercover 84, it is usually advantageous to place the nonwoven side facing out away from the user. In addition, in such embodiments it may be possible to utilize the nonwoven portion of the laminate 32 as the loop portion of the hook and loop combination.

Other uses for the film and film/nonwoven laminates according to the present invention include, but are not limited to, surgical drapes and gowns, wipers, barrier materials and garments/articles of clothing or portions thereof including such items as workwear and lab coats.

It has previously been found that calcium carbonate filled KRATON films produce little to no breathability but have excellent elastic properties after stretch-thinning while calcium carbonate filled polyethylene plastomer films produce breathability but have insufficient stretch properties. As a result, tests were conducted to determine if a mixture of both materials would produce a film having a desirable balance between breathability and elastic properties.

A series of film trials and lamination trials were conducted to produce materials for evaluation. For the first film trial, styrene block copolymers and mixed density polyethylene plastomers were compounded with various levels of calcium carbonate filler as follows:

45% KRATON G1730, 55% $CaCO_3$ (1730-45)
25% KRATON G1657, 75% $CaCO_3$ (1657-25)
25% KRATON G1730, 75% $CaCO_3$ (1730-25)
20% AFFINITY PL1845/20% AFFINITY EG 8200, 60% $CaCO_3$ (P4592-106A)

Materials were melt blended at the ratios shown in Table 1. A 100 gram/square meter (gsm) single film layer was produced for each composition except the last one made with 100% of 25% KRATON G 1730, 75% $CaCO_3$. Efforts regarding this last sample were aborted due to the formation of numerous holes in the film which may have been due to moisture absorption. The materials were melted at temperatures up to about 435° F. In addition, the extruder die gap was also reduced from 0.05" to 0.038".

TABLE 1

| Sample | Film | P4592-106A | 1730-45 | 1657-25 | 1730-25 |
|---|---|---|---|---|---|
| 1 | XP1823A | 50% | 50% | — | — |
| 2 | XP1823B | 25% | 75% | — | — |
| 3 | XP1823C | — | 100% | — | — |
| 4 | XP1823D | 50% | — | 50% | — |
| 5 | XP1823E | 25% | — | 75% | — |
| 6 | XP1823F | — | — | 100% | — |
| 7 | XP1823G | — | — | — | 100% |

Most of the above samples were collected as film rolls. However, when the time came for stretching and laminating them, only samples 1 and 2 could be sucessfully stretched and laminated. Both samples were adhesively laminated to two different CD deformable spunbond web materials, a 45% necked/polypropylene (PP) spunbond and a 70/30 PP/flexible polyolefin (FPO) bicomponent (Bico) spunbond (SB). The resulting stretch conditions for each film were different because sample 1 could be stretched to a higher ratio than sample 2. The films were laminated by a method that allowed the resulting laminate to exhibit both MD and CD stretch. This was achieved by adhesively laminating the spunbond to the tensioned film while it was elongated. The laminate was then allowed to retract completely before winding onto a roll. A 3 gsm add-on of Findley 2525A, a styrene block copolymer adhesive available from Findley Adhesives, Inc. of Wauwatusa, Wis., was used.

Laminates were produced in accordance with the data shown in Table 2.

TABLE 2

| Sample | Film | Spunbond Type | Stretch Ratio |
|---|---|---|---|
| 1 | XP1823A | 45% Necked PP | 5.5× |
| 2 | XP1823A | 0.8 osy 70/30 PP/FPO Bicomponent | 5.0× |
| 3 | XP1823B | 0.8 osy 70/30 PP/FPO Bicomponent | 4.0× |
| 4 | XP1823B | 45% Necked PP | 4.0× |
| 5 | XP1823B | 45% Necked PP | 4.5× |

Table 3 sets forth the results of tests conducted on these laminates.

TABLE 3

| Sample | WVTR Avg. | Hyst Avg. 50% Ult Elong @ 30% CD | Set % CD @ 30% | Hyst Avg. 100% Ult Elong @ 50% CD | Set % CD @ 50% |
|---|---|---|---|---|---|
| XP1823A/45% Necked SB (5.5×) | 2398 | 73.1 | 14.1 | 89.7 | 30 |
| XP1823A/FPO Bico SB (5.0×) | 2064 | 59.1 | 10 | 81.9 | 18 |
| XP1823B/FPO Bico SB (4.0×) | 73 | 64.6 | 11.2 | 80.7 | |
| XP1823B/45% Necked SB (4.0×) | 123 | 73.1 | 12 | 94.5 | |
| XP1823B/45% Necked SB (4.5×) | 113 | 74.4 | 13.9 | 92.9 | |

Overall, the test results show that greater breathability was attained with the samples having the higher filled PE (XP1823A) level, and the elastic stretch and recovery was sufficient for the needs of a CD/MD stretchable garment. In the case of the higher filled KRATON sample (XP1823B), the breathability was very low. This indicates that a certain percent of metallocene-catalyzed plastomer LLDPE should be in the total mixture so that the micropores can remain open to provide breathability.

Breathability was also found to be a function of the level of stretch. As the stretch ratio increased, breathability increased. These results indicate that at least 5× stretch is desirable for the XP1823A formulation to provide a WVTR above 2000 g/m²/24 hours. To obtain a WVTR greater than 3000 g/m²/24 hours, stretch ratios of greater than 5× are desirable. Acceptable breathability could not be obtained from the XP1823B sample even at the highest stretch level of 4.533. Beyond the 4.5× stretch level, the material would break out in the MDO.

Due to the favorable results obtained using these laminates, an XP1823A film roll was stretched again on an MDO/laminator at higher stretch ratios to improve breathability. During this second lamination trial, three different types of CD-deformable spunbond, as shown in Table 4, were evaluated. The stretch ratios evaluated were between 5–633. The three CD-deformable spunbonds consisted of 45% necked PP spunbond, a 70/30 PP/FPO spunbond and a bicomponent PP/nylon spunbond which had been processed through a grooved roll process. The grooved roll process, such as is available from Biax Fiberfilm Corporation of Neenah, Wis., is a process whereby the spunbond is mashed through intermeshing grooved rolls which break the bond points of the spunbond and allow it to stretch more fully in the cross machine direction. Results from this trial, shown in Table 5, provided information on the better CD-deformable spunbond as well as the effects of high stretch ratios on breathability and stretch properties.

TABLE 4

| Sample | Film | Spunbond Type | Stretch Ratio |
|---|---|---|---|
| 1 | XP1823A | Grooved Roll Bicomponent | 6.0× |
| 2 | XP1823A | Grooved Roll Bicomponent | 5.5× |
| 3 | XP1823A | Grooved Roll Bicomponent | 5.0× |
| 4 | XP1823A | 70/30 PP/FPO Bicomponent | 6.0× |
| 5 | XP1823A | 70/30 PP/FPO Bicomponent | 5.5× |
| 6 | XP1823A | 70/30 PP/FPO Bicomponent | 5.0× |
| 7 | XP1823A | 45% Necked PP | 6.0× |
| 8 | XP1823A | 45% Necked PP | 5.5× |
| 9 | XP1823A | 45% Necked PP | 5.0× |

The results of this lamination trial confirmed that the higher the stretch ratio of the film, the higher the breathability results for the laminate. Increasing the stretch ratio to 633, also produced WVTR results over 3000 g/m²/24 hours, which is a preferred target for high breathability. The increased stretch ratio, however, does slightly decrease the elastic recovery (CD hysteresis at 50 and 30%) and increase the % set of the laminate. This is, however, a very small loss in elastic recovery when compared to the increase in breathability that is obtained from increasing stretch ratio.

TABLE 5

| SAMPLE | WVTR Avg. | Hyst Avg. 100% Ult Elong @ 50% CD | Set % CD @ 50% | Hyst Avg. 50% Ult Elong @ 30% CD | Set % CD @ 30% |
|---|---|---|---|---|---|
| XP1823A/Grooved Roll Bicomponent SB (6×) | 3211 | 85.64 | 33.15 | 73.58 | 11.98 |
| XP1823A/Grooved Roll Bicomponent SB (5.5×) | 2757 | 83.48 | 32.87 | 68.06 | 11.28 |
| XP1823A/Grooved Roll Bicomponent SB (5.0×) | 2456 | 84.54 | 32.16 | 68.14 | 10.6 |
| XP1823A/FPO Bico SB (6×) | 3052 | 80.12 | 29.13 | 61.98 | 9.68 |
| XP1823A/FPO Bico SB (5.5×) | 2581 | 80.16 | 28.68 | 61.54 | 9.56 |
| XP1823A/FPO Bico SB (5×) | 2227 | 78.2 | 26.52 | 60.62 | 9.36 |
| XP1823A/45% Necked SB (6×) | 3032 | 87.3 | 36.84 | 67.98 | 11 |
| XP1823A/45% Necked SB (5.5×) | 2948 | 89.06 | 36.09 | 69.74 | 10.76 |
| XP1823A/45% Necked SB (5×) | 2594 | 87.82 | 35.07 | 67.56 | 10.2 |

There was no significant difference in the breathability based upon the different spunbond facing types. However, the type of spunbond facing did affect the elastic property results as indicated by the 100% CD stretch results. The 70/30 PP/FPO stretchable bicomponent spunbond produced the preferred elastic properties. The hysteresis results at MDO stretch ratios between 5–6× were about 78–80% and the % set was between 26–29%. These results were much better than the results for the grooved roll spunbond and the necked spunbond facings. The extension tension results (data not shown) were also lower for the bicomponent FPO facing than the other two facings. These results indicate that the FPO spunbond is more CD-deformable than the other spunbond facings. It appears to demonstrate less resistance to CD-stretch at levels as high as 100% as indicated by the lower extension tension results. The hysteresis and % set results also indicate that this facing material has some elastic retraction properties that add to the retraction of the film in the laminate.

After the second lamination trial, a second film trial was carried out for the purpose of attaining breathability above about 3000 WVTR. In this trial, higher total levels of calcium carbonate filler were evaluated as well as different types of KRATON block copolymers and different ratios of the KRATON filled compounds to the metallocene (met)-catalyzed polyethylene (PE) filled compound. For this trial, the following materials were employed:

QST P5492-95A–55% Supercoat CaCO₃ (available from ECC International, Atlanta, Ga.)+45% mixture of met PE resins (Dow AFFINITY PL1845 and EG8200)

QST P5492-106A–60% Supercoat CaCO₃+40% mixture of met PE resins (Dow AFFINITY PL1845 and EG8200)

SCC 18897–60% Supercoat CaCO₃+40% KRATON G1730 tetrablock

SCC 18898–60% Supercoat CaCO₃+40% KRATON G2760 triblock

SCC 27410–75% Supercoat CaCO₃+Dow 2553 LLDPE (40MI) (a conventional Zeigler-Natta catalyzed LLDPE)

QST 1657-25–75% Supercoat CaCO₃+25% KRATON G1657 triblock.

Blends of these materials at different ratios were made into single layer films at an 80 gsm basis weight target as shown in Table 6.

TABLE 6

| Sample | CODE | % CaCO₃ | % Kraton | % PE | SCC 18897 | QST 1657-25 | SCC 18898 | P549 2-106A | P549 2-95A | SCC 27410 |
|---|---|---|---|---|---|---|---|---|---|---|
| 1 | A | 57.5 | 20 | 22.5 | 50% | | | | 50% | |
| 2 | B | 58 | 24 | 18 | 60% | | | | 40% | |
| 3 | C | 60 | 20 | 20 | 50% | | | 50% | | |
| 4 | D | 60 | 24 | 16 | 60% | | | 40% | | |
| 5 | E | 65 | 12.5 | 22.5 | | 50% | | | 50% | |
| 6 | F | 67 | 15 | 18 | | 60% | | | 40% | |
| 7 | G | 57.5 | 20 | 22.5 | | | 50% | | 50% | |
| 8 | H | 58 | 24 | 18 | | | 60% | | 40% | |
| 9 | I | 58.5 | 28 | 13.5 | | | 70% | | 30% | |
| 10 | J | 57 | 16 | 27 | | | 40% | | 60% | |
| 11 | K | 67.5 | 20 | 12.5 | | | 100% | | | |
| 12 | L | 67.5 | 20 | 12.5 | | | 50% | | | 50% |
| 13 | M | 69 | 16 | 15 | 50% | | | | | 50% |
| 14 | N | 100 | | | | 100% | | | | |
| | CONTROL XP1823A | 57.5 | 22.5 | 20 | | | | | | |

Most of the films were able to be collected successfully. There were some problems with die lip build-up (accumulation of polymeric material at the die exit) on some of the samples, as well as issues related to pinning the materials to a cast roll due to uneven flow on the edges due to poor melt strength, resulting in break away of the film exiting the die. In addition, because the P5492-95A material had not been dried well enough, there was evidence of lensing spots (water spots) seen in those films made with that material. Some films had a slightly mottled appearance as if the two different compounds were not well mixed. However, samples 12 and 13 were not collected because the materials did not mix well at all. The film was very brittle and often had holes as it came off the die. Distinct separations were noticeable between the KRATON material and the LLDPE. This was an indication that the KRATON does not melt mix well with a conventional Zeigler-Natta catalyzed LLDPE. In order to produce the necessary well-dispersed melt mixed precursor film, the metallocene-catalyzed LLDPE plastomers are preferably used with the KRATON styrene block copolymer. Samples 5 and 6 experienced excessive die build-up which sloughed off and caused holes in the film. As a result, only small rolls were collected of these samples.

The total calcium carbonate percentage employed in the samples shown in Table 6 varied between about 57.5% and about 69%. The percent KRATON in the blends ranged from about 12.5% to about 30% with the met PE percentage being in the range of about 12.5% to about 27%.

The films that were produced were then adhesively laminated on an MDO to a 0.8 osy 70/30 FPO/spunbond. The films were again laminated so that the laminate could be stretched in both the machine direction and the cross machine direction. This was achieved by adhesively laminating the spunbond to the tensioned film while it was elongated after which the laminate was allowed to retract completely prior to winding. The films were stretched between about 3.5x to about 5.0x.

Most of the films were laminated. However, problems were encountered with samples 6, 8, 9, 11 and 14. Samples 6, 8 and 9 frequently broke during stretching due to the light spots and holes caused from the lensing from the P5492-95A resin. Samples 11 and 14 broke out of the MDO due to too much tension during stretching because these samples contained only KRATON and no met PE. This was another example of the need for the metallocene-catalyzed LLDPE addition in the blend to reduce the high tension force attributed to the high elasticity of the KRATON. Only samples 1–5,7, and 10 were successfully laminated and tested to give results.

Table 7 presents elasticity values and breathability for the samples in Table 6.

TABLE 7

| SAMPLE | 100% Elong Hyst @ 50% | % Set | 50% Elong Hyst @ 30% | % Set | WVTR g/m²/24 hr |
|---|---|---|---|---|---|
| A at 3.5x | 81.6 | 26.09 | 63.8 | 10.8 | 1301 |
| A at 4.0x | 84.9 | 28.12 | 64.9 | 10.9 | 2144 |
| A at 4.5x | 85.1 | 28.68 | 65.4 | 11.1 | 2728 |
| A at 4.75x | 85.9 | 29.22 | 66.3 | 11.8 | 3113 |
| B at 3.5x | 84.4 | 25.88 | 65.7 | 11.4 | 1597 |
| B at 4.0x | 85.3 | 26.4 | 97 | 11 | 1789 |
| B at 4.5x | 85.4 | 27.95 | 67 | 11.1 | 2338 |
| B at 4.75x | 85.2 | 27.23 | 68.4 | 12.3 | 2559 |
| C at 3.5x | 84.1 | 25.84 | 65.8 | 11.5 | 2307 |
| C at 4.0x | 84.2 | 26.37 | 66.1 | 11.8 | 2641 |
| C at 4.5x | 85.8 | 29.12 | 66.5 | 12.1 | 3260 |
| C at 4.75x | 85.6 | 28.53 | 65 | 10.4 | 3045 |
| C at 5.0x | 85.7 | 28.62 | 65.7 | 10.1 | 3075 |
| D at 3.5x | 84.1 | 25.7 | 64.4 | 9.3 | 1693 |
| D at 4.0x | 84.3 | 26 | 63.6 | 8.5 | 2236 |
| D at 4.5x | 85.4 | 28.3 | 65.3 | 8.6 | 2779 |
| D at 4.75x | 85.1 | 28.29 | 64.3 | 8.6 | 2876 |
| G at 3.5x | 88.2 | 34.26 | 67.6 | 10.9 | 1763 |
| G at 4.0x | 89 | 35.9 | 68.2 | 8.3 | 2110 |
| G at 4.5x | 90.3 | 37.14 | 69.3 | 0* | 2729 |
| G at 4.75x | 90.2 | 36.73 | 67.5 | 4 | 2698 |
| G at 5.0x | 89.9 | 37 | 66.9 | 0* | 2990 |
| H at 3.5x | 87.9 | 32.22 | 67.2 | 0* | 585 |
| H at 4.0x | 87.6 | 32.28 | 66.6 | 0* | 1632 |
| I at 3.5x | 84.6 | 29.11 | 66 | 0* | 439 |
| I at 4.0x | 86.2 | 30.79 | 65.3 | 0* | 1332 |
| I at 4.5x | 88.9 | 32.12 | 71.5 | 13.4 | 2259 |
| I at 4.75x | 88.1 | 31.33 | 69.5 | 12.4 | 2418 |
| I at 5.0x | 88.7 | 31.65 | 69.2 | 11.8 | 2822 |
| J at 3.5x | 89.7 | 36.51 | 70.3 | 13.7 | 1280 |
| J at 4.0x | 89.9 | 36.88 | 70.3 | 13.4 | 1879 |
| J at 4.5x | 89.7 | 37.07 | 71 | 13.5 | 2433 |
| J at 4.75x | 89.7 | 37.39 | 70.4 | 14.1 | 2690 |
| J at 5.0x | 90.5 | 38.68 | 71.8 | 14.2 | 2913 |

*Test failed to record information

Overall results are summarized below.

The breathability (WVTR) significantly improved with the increased MDO stretch ratio. In many cases, as the stretch ratio went from 3.5 to 5x, the WVTR doubled.

As the CaCO₃ loading increased from a low of 57% to 60% with the same ratio of KRATON to met PE, the WVTR only slightly increased. However, this is a very small range of variance in the loading, which might explain the insignificant difference. Desired breathabilities were obtained for some of the codes within these ranges of calcium carbonate.

Elastic properties increased with the percent KRATON, but often at the expense of the breathability (WVTR). Also at the higher KRATON levels, too much stretching tension resulted and often the film tended to break out while stretching on the MDO. With the increase in the percent of metallocene-catalyzed PE in the blends, the elastic properties decreased, especially the CD %set. Little to no effect on the elasticity was attributed to the increase in % filler. This again may be due to the small range of calcium carbonate levels that were evaluated in this experiment.

The KRATON G1730 did perform better than the KRATON G2760. Most blends produced with the G2760 produced lower elastic properties as well as lower WVTR results in comparison to the G1730. This was unexpected because these properties typically demonstrate an indirect relationship to each other.

All results considered, the better performer from this experiment was the C code material, although it was comparable to the A code material. Higher WVTR was obtained at lower stretch ratios with the C code material while the elastic properties remained comparable. However, compared to the XP1823A from the previous trial, the XP1823A hysteresis results were better. The XP1823A code material was not reproduced during this trial because this experiment used mixtures of two precompounded materials dry blended just prior to film extrusion. Therefore, the same resin ratios as in the XP1823A code material from the previous trial could not be obtained.

The conclusion from all experiments with these formulations is that the preferred ratio of KRATON to metallocene-catalyzed LLDPE resin is at close to a 50/50 ratio. At this ratio, there appears to be enough of a balance between the elastic stretch and recovery property vs. the breathability. Any significant change from the 50/50 ratio in either direction results in a loss of breathability, elastic recovery or processing issues while stretching on the MDO. With this in mind, one preferred film formulation comprises about 58% $CaCO_3$+21% KRATON G1730+21% mix of metallocene-catalyzed LLDPE plastomers stretched to 5× on an MDO.

Notwithstanding, a material having a substantially lesser amount of KRATON relative to the amount of metallocene-catalyzed LLDPE plastomer having acceptable stretch and breathability properties was produced. In this case, the film formulation had 58% $CaCO_3$, 10.5% KRATON and 31.5% of a mix of metallocene-catalyzed LLDPE plastomers. The basis weight of the material was 69.5 gsm on a pre-stretched basis and 21.7 gsm after having been stretched. The resulting film had a WVTR of about 4427 $g/m^2/24$ hours and a laminate employing this film had a WVTR of about 4482 $g/m^2/24$ hours.

Test Procedures

WVTR: The water vapor transmission rate (WVTR) for the sample materials was calculated in accordance with ASTM Standard E96-80. Circular samples measuring three inches in diameter were cut from each of the test materials and a control which was a piece of CELGARD® 2500 film from Hoechst Celanese Corporation of Sommerville, N.J. CELGARD® 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at about 100EF (38 EC) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed and immediately returned to the oven. After 24 hours, the pans were removed from the oven and weighed again. The preliminary test water vapor transmission rate values were calculated with Equation (I) below:

(I) Test WVTR=(grams weight loss over 24 hours)×315.5 g/m2/24 hours

The relative humidity within the oven was not specifically controlled.

Under the predetermined set conditions of about 100° F. (38° C.) and ambient relative humidity, the WVTR for the CELGARD® 2500 control has been defined to be 5000 grams per square meter for 24 hours. Accordingly, the control sample was run with each test and the preliminary test values were corrected to set conditions using Equation (II) below:

(II) WVTR=(Test WVTR/control WVTR)×(5000 $g/m^2$/24 hours)

Extension/Retraction: Sintech tests included a two-cycle, 50 percent ultimate (target) elongation extension test (that is a predefined point of elongation) with the first cycle extension tension and second cycle retraction tension taken at 30 percent, and a two cycle, 100 percent extension test with a first cycle extension tension and second cycle retraction tension taken at 50 percent. For the 50 percent ultimate elongation extension test, the sample is first elongated to an ultimate elongation of 50 percent and then allowed to retract/recover to an amount where the amount of resistance is zero. Testing is done on the Sintech 1/S or 2/S equipment utilizing TESTWORKS for Windows 3.02 software to record data. In conducting an extension/retraction test, a 3 inch wide sample of the material is held within clamps (3 inch gauge length for 100 percent and 4 inch gauge length for 50 percent) and pulled to a target elongation of either 50, or 100 percent at a rate of 500 mm/min, and returned to the original distance, typically of four inches, for two cycles. The test was done at ambient temperature and humidity conditions.

Hysteresis is calculated in accordance with the following equation:

$$\text{Hysteresis} = \frac{\text{Force of Extension (1}^{st}\text{ cycle)} - \text{Force of Retraction (2}^{nd}\text{ cycle)}}{\text{Force of Extension (1}^{st}\text{ cycle)}} \times 100$$

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A breathable, stretch-thinned elastic film, comprising:
   a high performance styrene block copolymer elastomer;
   a low performance metallocene catalyzed polyolefin elastomer;
   the high and low performance elastomers being present in a weight ratio of about 50–80 parts by weight high performance elastomer and about 20–50 parts by weight low performance elastomer, based on a combined weight of high and low performance elastomers; and
   a plurality of filler particles;
   the film having a water vapor transmission rate of at least about 1000 grams/m$^2$/24 hours.

2. A breathable, stretch-thinned elastic film comprising:
   a high performance styrene block copolymer elastomer;
   a low performance ethylene copolymer elastomer having a density less than 0.90 grams/cm$^3$;
   the high and low performance elastomers being present in a weight ratio of about 50–80 parts by weight high performance elastomer and about 20–50 parts by weight low performance elastomer, based on a combined weight of high and low performance elastomers; and
   a plurality of filler particles;
   the film having a water vapor transmission rate of at least about 1000 grams/m$^2$/24 hours.

3. The breathable, stretch-thinned film of claim 1 or 2, wherein the styrene block copolymer elastomer comprises a tetrablock copolymer.

4. The breathable, stretch-thinned film of claim 1 or 2, wherein the styrene block copolymer elastomer comprises a diblock copolymer.

5. The breathable, stretch-thinned film of claim 1 or 2, wherein the low performance elastomer comprises an ethylene-alpha olefin copolymer in which the alpha-olefin is selected from the group consisting of 1-octene, 1-butene, 1-hexene and 4-methyl pentene.

6. The breathable, stretch-thinned film of claim 5, wherein the low performance elastomer has a density of about 0.86–0.89 grams/cm$^3$.

7. The breathable, stretch-thinned film of claim 1 or 2, wherein the filler particles comprise inorganic filler particles.

8. The breathable, stretch-thinned film of claim 7, wherein the filler particles comprise calcium carbonate.

9. The breathable, stretch-thinned film of claim 1 or 2, comprising greater than about 50% by weight of the filler particles.

10. The breathable, stretch-thinned film of claim 1 or 2, comprising about 51–70% by weight of the filler particles.

* * * * *